(12) United States Patent  
O'Phelan et al.

(10) Patent No.: US 6,684,102 B1  
(45) Date of Patent: Jan. 27, 2004

(54) IMPLANTABLE HEART MONITORS HAVING CAPACITORS WITH ENDCAP HEADERS

(75) Inventors: Michael J. O'Phelan, Oakdale, MN (US); Robert R. Tong, Valencia, CA (US); Luke J. Christenson, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 130 days.

(21) Appl. No.: 09/706,515

(22) Filed: Nov. 3, 2000

(51) Int. Cl.[7] ............................................. A61N 1/32

(52) U.S. Cl. ............................ 607/5; 607/9; 607/20; 607/101; 607/109

(58) Field of Search ........................... 607/1–5, 9, 20, 607/25, 101, 119

(56) References Cited

U.S. PATENT DOCUMENTS

| | | | |
|---|---|---|---|
| 3,643,168 A | 2/1972 | Manicki | 325/459 |
| 3,723,926 A | 3/1973 | Thomas et al. | 335/268 |
| 3,777,570 A | 12/1973 | Thomas et al. | 73/398 |
| 3,826,143 A | 7/1974 | Thomas et al. | 73/398 C |
| 3,828,227 A | 8/1974 | Millard et al. | 317/230 |
| 3,859,574 A | 1/1975 | Brazier | 317/230 |
| 3,938,228 A | 2/1976 | Kemkers et al. | 29/25.42 |
| 4,047,790 A | 9/1977 | Carino | 339/220 |
| 4,088,108 A | 5/1978 | Hager | 123/148 CC |
| 4,131,935 A | 12/1978 | Clement | 361/433 |
| 4,571,662 A | 2/1986 | Conquest et al. | 361/306 |
| 4,782,340 A | 11/1988 | Czubatyj et al. | 340/825.83 |
| 5,131,388 A | 7/1992 | Pless et al. | 128/419 D |
| 5,471,087 A | 11/1995 | Buerger, Jr. | 257/532 |
| 5,522,851 A | 6/1996 | Fayram | 607/5 |
| 5,554,178 A | 9/1996 | Dahl et al. | 607/122 |
| 5,584,890 A | 12/1996 | MacFarlane et al. | 29/25.03 |
| 5,628,801 A | 5/1997 | MacFarlane et al. | 29/25.03 |
| 5,660,737 A | 8/1997 | Elias et al. | 216/6 |
| 5,754,394 A | 5/1998 | Evans et al. | 361/516 |
| 5,779,699 A | 7/1998 | Lipson | 606/41 |
| 5,779,891 A | 7/1998 | Andelman | 210/198.2 |
| 5,800,724 A | 9/1998 | Habeger et al. | 216/35 |
| 5,908,151 A | 6/1999 | Elias | 228/110.1 |
| 5,922,215 A | 7/1999 | Pless et al. | 216/6 |
| 5,926,357 A | 7/1999 | Elias et al. | 361/302 |

(List continued on next page.)

FOREIGN PATENT DOCUMENTS

| | | | |
|---|---|---|---|
| WO | WO-98/27562 | 6/1998 | H01G/4/18 |
| WO | WO-99/51302 | 10/1999 | A61N/1/375 |
| WO | WO-00/19470 | 4/2000 | H01G/9/055 |

Primary Examiner—Hieu T. Vo  
Assistant Examiner—Johnny H. Hoang  
(74) Attorney, Agent, or Firm—Schwegman, Lundberg, Woessner & Kluth, P.A.

(57) ABSTRACT

Implantable heart-monitoring devices, such as defibrillators, pacemakers, and cardioverters, detect onset of abnormal heart rhythms and automatically apply corrective electrical therapy, specifically one or more bursts of electric charge, to abnormally beating hearts. Critical parts in these devices include the capacitors that store and deliver the bursts of electric charge. Some devices use cylindrical aluminum electrolytic capacitors which include terminal that extend from one end of the case, making the capacitor longer than it otherwise would be and generally necessitating use of larger implantable device housings. Accordingly, the inventors devised unique capacitor connection structures that allow size reduction. One exemplary capacitor includes two conductive endcaps at opposite ends of its capacitive element, instead of two upright terminals at one end, thereby allowing reduction in the height or volume of the capacitor and/or increases in the dimensions of other components, such as aluminum foils. Other aspects of the invention include heart-monitoring devices that incorporate the unique capacitors.

17 Claims, 5 Drawing Sheets

U.S. PATENT DOCUMENTS

| | | | |
|---|---|---|---|
| 5,930,109 A | 7/1999 | Fishler | 361/508 |
| 5,963,418 A | 10/1999 | Greenwood, Jr. et al. | 361/508 |
| 5,968,210 A | 10/1999 | Strange et al. | 29/25.03 |
| 5,973,906 A | 10/1999 | Stevenson et al. | 361/302 |
| 5,983,472 A | 11/1999 | Fayram et al. | 29/25.42 |
| 6,002,969 A | 12/1999 | Machek et al. | 607/122 |
| 6,006,133 A | 12/1999 | Lessar et al. | 607/5 |
| 6,009,348 A | 12/1999 | Rorvick et al. | 607/5 |
| 6,032,075 A | 2/2000 | Pignato et al. | 607/5 |
| 6,040,082 A | 3/2000 | Haas et al. | 429/163 |
| 6,042,624 A | 3/2000 | Breyen et al. | 29/25.03 |
| 6,052,625 A | 4/2000 | Marshall | 607/122 |
| 6,094,788 A | 8/2000 | Farahmandi et al. | 25/24.41 |
| 6,099,600 A | 8/2000 | Yan et al. | 29/25.03 |
| 6,104,961 A | 8/2000 | Conger et al. | 607/122 |
| 6,110,233 A | 8/2000 | O'Phelan et al. | 29/25.03 |
| 6,118,651 A | 9/2000 | Mehrotra et al. | 361/509 |
| 6,141,205 A | 10/2000 | Nutzman et al. | 361/509 |
| 6,157,531 A | 12/2000 | Breyen et al. | 361/519 |
| 6,184,160 B1 | 2/2001 | Yan et al. | 438/800 |
| 6,191,931 B1 | 2/2001 | Paspa et al. | 361/302 |
| 6,212,063 B1 | 4/2001 | Johnson et al. | 361/517 |
| 6,249,423 B1 | 6/2001 | O'Phelan et al. | 361/502 |
| 6,249,709 B1 | 6/2001 | Conger et al. | 607/122 |
| 6,256,542 B1 | 7/2001 | Marshall et al. | 607/126 |
| 6,259,954 B1 | 7/2001 | Conger et al. | 607/122 |
| 6,275,729 B1 * | 8/2001 | O'Phelan et al. | 607/5 |
| 6,297,943 B1 | 10/2001 | Carson | 361/500 |
| 6,299,752 B1 | 10/2001 | Strange et al. | 205/152 |
| 6,321,114 B1 | 11/2001 | Nutzman et al. | 607/5 |
| 6,326,587 B1 | 12/2001 | Cardineau et al. | 219/121.68 |
| 6,388,866 B1 | 5/2002 | Rorvick et al. | 361/503 |
| 6,402,793 B1 | 6/2002 | Miltich et al. | 29/25.03 |
| 6,442,015 B1 | 8/2002 | Niiori et al. | 361/502 |
| 6,477,037 B1 | 11/2002 | Nielsen et al. | 361/520 |
| 6,493,212 B1 | 12/2002 | Clarke et al. | 361/521 |

\* cited by examiner

IMPLANTABLE HEART MONITORS HAVING CAPACITORS WITH ENDCAP HEADERS

CROSS-REFERENCE TO RELATED APPLICATIONS

This application is related to commonly assigned application Ser. No. 09/706,447, filed on even date herewith, entitled FLAT CAPACITOR FOR AN IMPLANTABLE MEDICAL DEVICE, which is incorporated herein by reference in its entirety.

FIELD OF THE INVENTION

The present invention concerns capacitors, particularly wet-electrolytic capacitors used in implantable medical devices, such as implantable defibrillators, cardioverters, and pacemakers.

The present invention concerns implantable heart monitors, such as defibrillators and cardioverters, particularly structures and methods for capacitors in such devices.

BACKGROUND

Since the early 1980s, thousands of patients prone to irregular and sometimes life-threatening heart rhythms have had miniature heart monitors, particularly defibrillators and cardioverters, implanted in their bodies. These devices detect onset of abnormal heart rhythms and automatically apply corrective electrical therapy, specifically one or more bursts of electric current, to hearts. When the bursts of electric current are properly sized and timed, they restore normal heart function without human intervention, sparing patients considerable discomfort and often saving their lives.

The typical defibrillator or cardioverter includes a set of electrical leads, which extend from a sealed housing into the walls of a heart after implantation. Within the housing are a battery for supplying power, monitoring circuitry for detecting abnormal heart rhythms, and a capacitor for delivering bursts of electric current through the leads to the heart.

The capacitor is often times a cylindrical aluminum wet electrolytic capacitor. This type capacitor usually includes stacked strips of aluminum foil and paper rolled, or wound, to form a cylindrical structure which is housed in a round tubular aluminum can. The can has an integral aluminum bottom end and an open top end sealed with a non-conductive flat circular lid, known as a header. Two terminals extend from the header, each connected to one of the rolled aluminum foils.

One problem the inventors recognized with these cylindrical capacitors is the overall height of the capacitor, measured from the bottom of the tubular aluminum can to the top of the terminals extending from the header. In particular, the terminals are rigid metal structures that generally require clearance space to avoid contacting other components within the housing of the implantable devices. Providing this clearance space ultimately increases the size of implantable devices beyond that otherwise necessary. Another related problem is that the diameter of the header has a practical minimum of about twelve millimeters and thus restricts how small capacitors and thus implantable devices can be made. Accordingly, the inventors identified a need to develop space-efficient techniques and structures for providing terminals on electrolytic capacitors.

SUMMARY OF THE INVENTION

To address this and other needs, the inventors devised wet electrolytic capacitors with unique connection structures. One exemplary capacitor includes two conductive endcaps at opposite ends of its capacitive element, instead of two upright terminals at one end, thereby allowing reduction in the height or volume of the capacitor and/or increases in the dimensions of other components, such as aluminum foils. Another exemplary capacitor includes two feedthrough assemblies at opposite ends of the wound capacitive element to also facilitate reduction in the height or volume of the capacitor or increasing its energy-storage density.

Other aspects of the invention include an implantable heart monitor, such as a pacemaker, defibrillator, congestive-heart-failure (CHF) device, or cardioverter defibrillator, that incorporates one or more capacitors with the unique connection structures.

DESCRIPTION OF THE PREFERRED EMBODIMENTS

The following detailed description, which references and incorporates FIGS. 1–5, describes and illustrates one or more specific embodiments of the invention. These embodiments, offered not to limit but only to exemplify and teach, are shown and described in sufficient detail to enable those skilled in the art to implement or practice the invention. Thus, where appropriate to avoid obscuring the invention, the description may omit certain information known to those of skill in the art.

Figure 1:
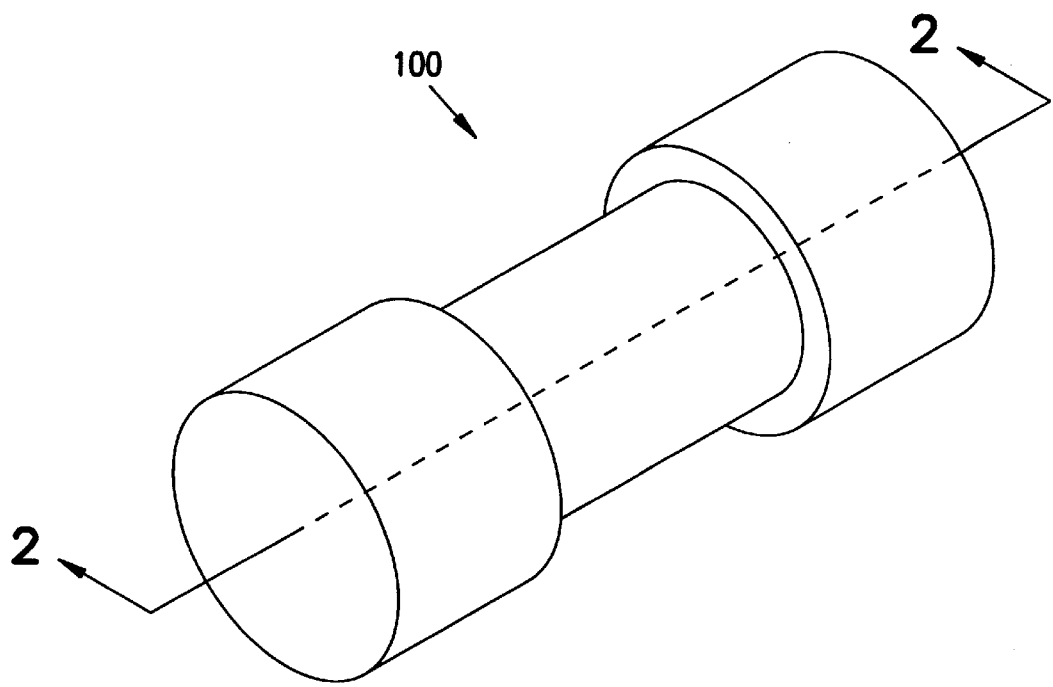
FIG. 1 is a perspective view of an exemplary cylindrical wet electrolytic capacitor 100 embodying teachings of the present invention.
Figure 2:
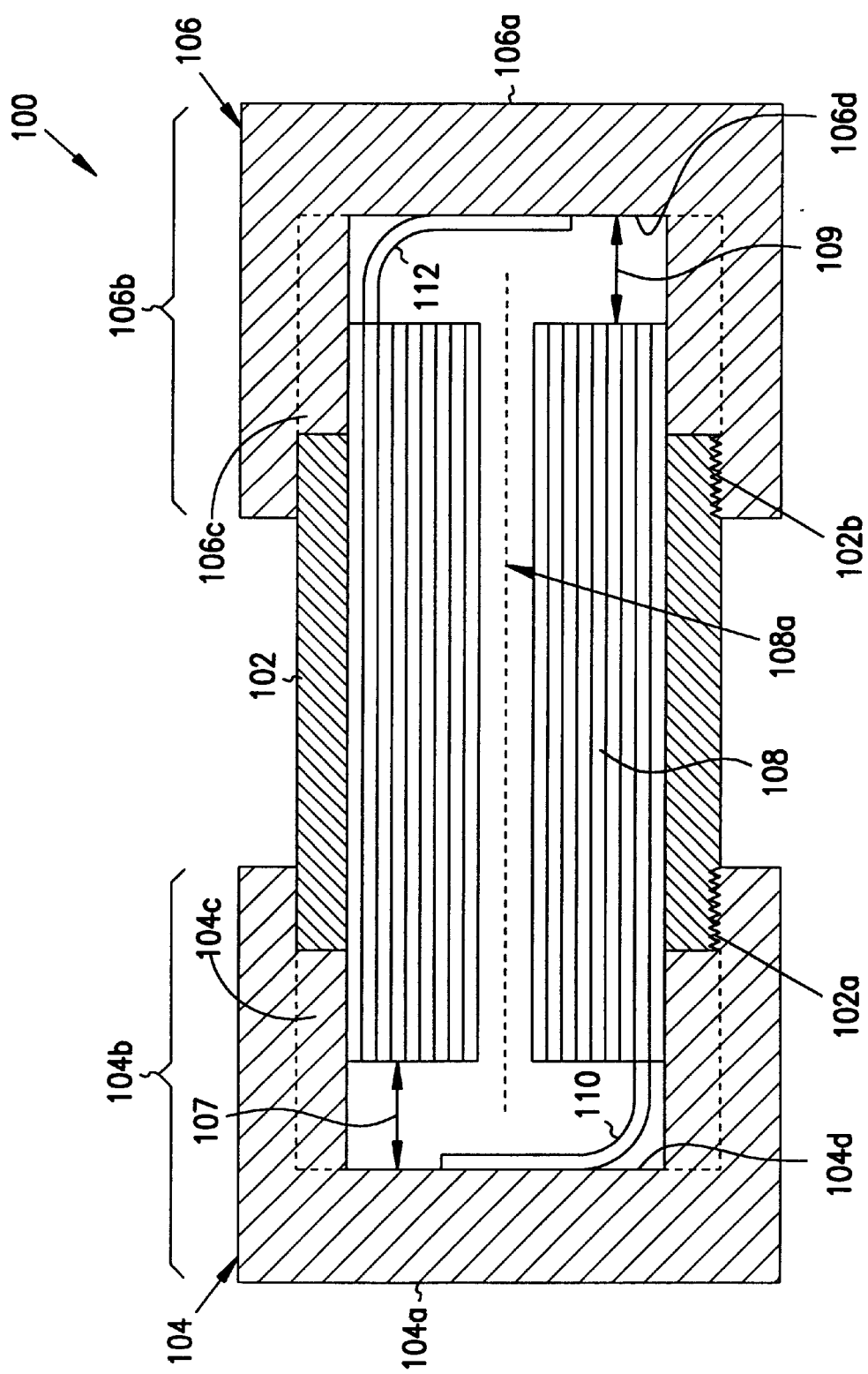
FIG. 2 is a cross-sectional view of capacitor 100 in FIG. 1 taken along line 2—2.

FIG. 1 shows a perspective view of an exemplary cylindrical wet electrolytic capacitor 100 which embodies teachings of the present invention. And, FIG. 2 shows a cross-section of capacitor 100 taken along line 2–2.

In particular, capacitor 100 includes a cylindrical or tubular section 102, cylindrical endcaps 104 and 106, a cylindrical capacitive element 108, anode tab 110, and cathode tab 112. Tubular section 102, which comprises a non-conductive material, such as a ceramic, a polymer, or a plastic, in the exemplary embodiment, at least partially encloses a central portion of wound or rolled capacitive element 108. To fully enclose capacitive element 108, section 102 has two opposing ends 102a and 102b that mate respectively with conductive end caps 104 and 106.

Endcaps 104 and 106, which are exemplarily formed of diecast (deep drawn) or machined aluminum or other conductive metal compatible with the capacitive element, are generally hemispherical or concave (cup-like) in structure, comprising respective planar end portions 104a and 106a and respective annular or tubular portions 104b and 106b. Tubular portions 104b and 106b have respective interior annular shoulders 104c and 106c, which abut respective ends 102a and 102b of tubular section 102, and also allow portions 104b and 106b to overlap corresponding portions of section 102. Thus, in this exemplary embodiment portions 104b and 106b mate with section 102 via a compound butt and lap joint. However, other embodiments omit annular shoulders 104c and 106c, and include threads on the interior of portions 104b and 106b and on the exterior of corresponding portions section 102. Other embodiments use other complementary joint structures and/or adhesives, epoxies, or other sealing compounds.

Endcap 104 is coupled via anode tab 110 to one or more anodic layers within capacitive element 108, and endcap 106 is coupled via cathode tab 112 to a second conductive layer within the capacitive element. More particularly, anode tab 110 contacts an interior surface 104d of endcap 104, and cathode tab 112 contacts an interior surface 106d of endcap 106. Interior surfaces 104d and 106d are separated by respective distances 107 and 109 from capacitive element 108 to prevent the tabs from shorting with other parts of the capacitive element.

In the exemplary embodiment, tabs 110 and 112 are welded respectively to surfaces 104d and 106d, and distances 107 and 109 are both approximately 0.02 inches (0.508 millimeters.) Some embodiments attach the tabs using conductive adhesives. Other embodiments reduce one or both of distances 107 and 109 by increasing the end margins of separators in capacitive element 108 and/or placing one or more insulative inserts between surface 104d and the capacitive element or between surface 106d and the capacitive element.

Figure 3:
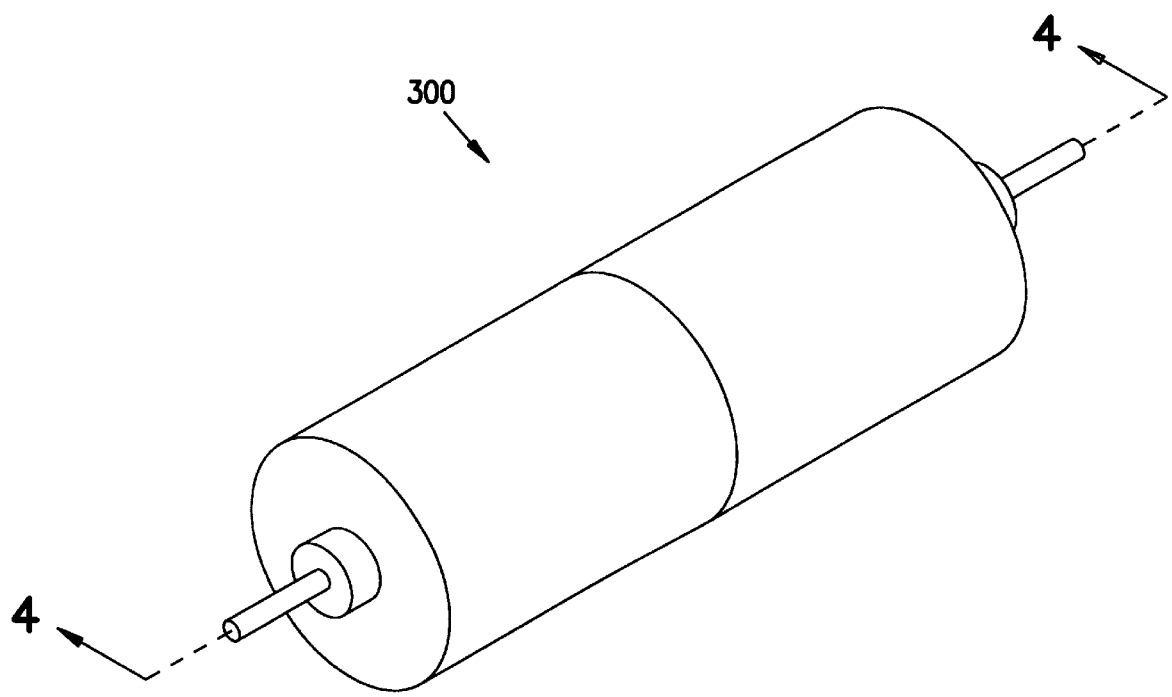
FIG. 3 is a perspective view of an exemplary cylindrical wet electrolytic capacitor 300 embodying teachings of the present invention.
Figure 4:
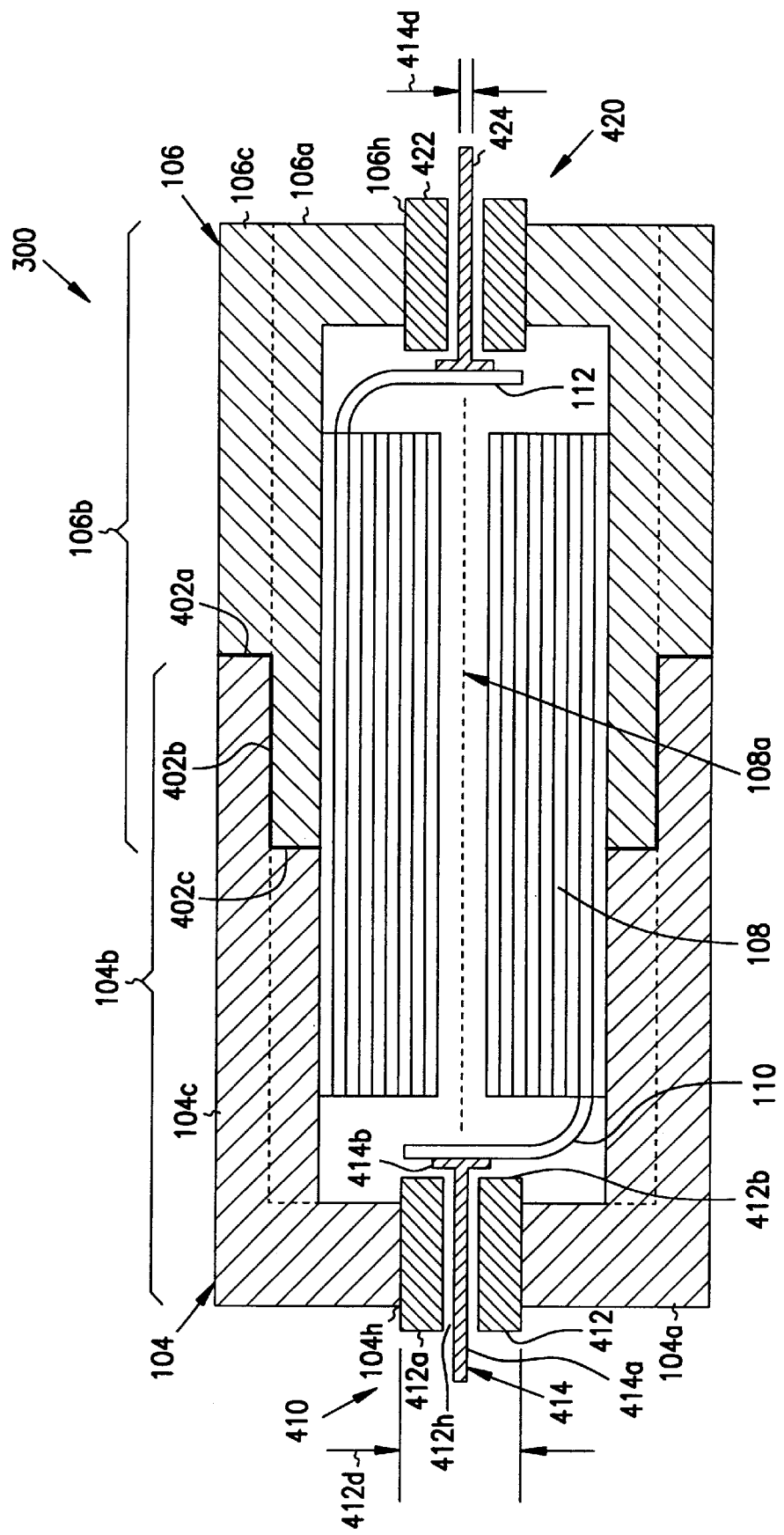
FIG. 4 is a cross-sectional view of capacitor 300 taken along line 4—4 in FIG. 3.

Capacitive element 108 includes an anode, a cathode, one or more inner separators, and two or more outer separators. The one or more inner separators are sandwiched between the anode and the cathode, and the resulting anode-separator-cathode sandwich is itself sandwiched between the outer separators. In the exemplary embodiment, the anode comprises three etched foils; the cathode comprises a single etched foil; and the separators comprise electrolyte-impregnated kraft paper. Exemplary foil materials include aluminum, tantalum, hafnium, niobium, titanium, zirconium, and combinations of these metals, and exemplary foil structures include core-etched, tunnel-etched, and perforated-core-etched foils. FIGS. 3 and 4 show an exemplary capacitor 300, which also embodies teachings of the present invention. Specifically, FIG. 3 shows a perspective view of capacitor 300, and FIG. 4 shows a cross-section of the capacitor taken along line 4—4.

In particular, capacitor 300, which is similar in many respects to capacitor 100 in FIGS. 1 and 2, includes cylindrical endcaps 104 and 106, cylindrical capacitive element 108, anode tab 110, and cathode tab 112. For sake of brevity, these aspects of capacitor 300 will be redescribed only where appropriate to highlight certain differences between the two exemplary embodiments.

Unlike capacitor 100, capacitor 300 omits tubular section 102, by forming a conductive interface 402 between endcaps 104 and 106. Endcaps 104 and 106 include respective planar end portions 104a and 106a and respective annular or tubular portions 104b and 106b. Tubular portions 104b include an interior annular shoulder 104c which mates with a complementary exterior annular shoulder 106c of tubular portion 106b, forming interface 402.

The exemplary embodiment seals an exterior portion 402a of the interface with an adhesive, such as an epoxy, or with a circumferential weld. Other embodiments, however, form middle portion 402b of the interface with threads on corresponding portions of tubular portions 104b and 106b. Still other embodiments omit annular shoulders 104c and 106c, welding, gluing, and or screwing tubular portions 104b and 106b together. Embodiments that omit shoulders 104c and 106c lack portions 402a and 402b of interface 402.

Planar end portions 104a and 106a include respective holes 104h and 106h for respective feedthrough assemblies 410 and 420. (Assemblies 410 and 420 are substantially identical in the exemplary embodiment, only assembly 410 is described here. However, some embodiments vary the assemblies appreciably still in keeping with one or more teachings of the invention.) Feedthrough assembly 410 includes a generally cylindrical insulative member 412 and a feedthrough conductor 414. Insulative member 412 includes an exterior face 412a, an interior face 412b, and a hole 412h which extends from face 412a to face 412b. Insulative member 412 has an exterior diameter (or more generally dimension) 412d for establishing an interference fit with hole 104h. In embodiments that construct insulative member 412 from glass or ceramic, the insulative member is secured in place by brazing the insulative member to the perimeter of hole 104h. (Some other embodiments weld a short metallic collar or sleeve to the case around the hole, insert the insulative member into the sleeve, and braze the insulative member to the sleeve and/or the feedthrough conductor. The sleeve can be made of aluminum or other metal compatible with the capacitor.)

Extending through hole 104h is a longitudinal shank portion 414a of feedthrough conductor 414. Shank portion 414a has a diameter or dimension 414d. Conductor 414a also has an integral disk-shaped head portion 414b which abuts interior face 412b of insulative member 412. An opposite side of head portion 414b is welded to anode tab 110, electrically coupling the feedthrough conductor to one or more anodes in capacitive element 108.

The exemplary embodiments forms insulative member 412 from glass, plastic, epoxy, or rubber and feedthrough conductor 414 from aluminum or other conductive material compatible with capacitive element 108. Additionally, it may be possible to size hole 104h, insulative member 412, hole 412h, and feedthrough conductor diameter 414d to cooperate with each other in establishing the interference fit between hole 104h and insulative member 412. Other embodiments epoxy the insulative member in place. Other embodiments mount the insulative member within hole 104h and apply an epoxy or other adhesive to secure and seal it in place. Still other embodiments mount the insulative member in a separate annular ring or collar having a flange, mount the annular ring into hole 104h and weld or braze the flange to planar portion 104a of the endcap.

Figure 5:
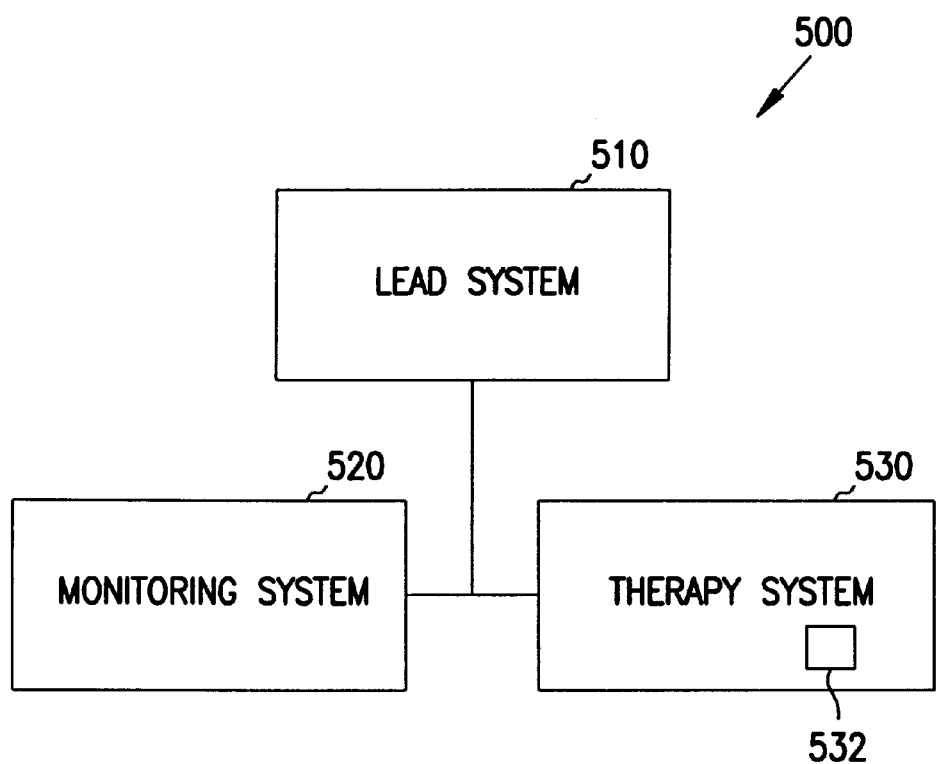
FIG. 5 is a block diagram of an exemplary implantable heart monitor 500 which includes one or more electrolytic capacitors 532 embodying teachings of the present invention.

FIG. 5 shows further details of the remaining portions of implantable heart monitor 500. Specifically, monitor 500 includes a lead system 510, which after implantation electrically contact strategic portions of a patient's heart, a monitoring circuit 520 for monitoring heart activity through one or more of the leads of lead system 510, and a therapy circuit 530 which includes one or more capacitors 532, each of which incorporates one or more teachings of capacitor 100 and/or 300. Monitor 500 operates according to well known and understood principles to perform defibrillation, cardioversion, pacing, and/or other therapeutic functions.

In addition to implantable defibrillators, congestive-heart-failure devices, and other cardiac rhythm management devices, such as pacemakers, the innovations of capacitor 100 can be incorporated into photographic flash equipment. Indeed, these innovations are pertinent to any application where compact, high-energy capacitors are desirable.

CONCLUSION

In furtherance of the art, the inventors have devised unique wet electrolytic capacitors for use in implantable heart monitors. One exemplary capacitor includes two conductive endcaps at opposite ends of its capacitive elements, instead of two upright terminals at one end, thereby allowing reduction in the height or volume of the capacitor and/or increases in the dimensions of other components, such as aluminum foils. Another exemplary capacitor includes two feedthrough assemblies at opposite ends of the wound capacitive element to also facilitate reduction in the height or volume of the capacitor or increase in its energy-storage density.

The embodiments described above are intended only to illustrate and teach one or more ways of practicing or implementing the present invention, not to restrict its breadth or scope. The actual scope of the invention, which embraces all ways of practicing or implementing the teachings of the invention, is defined only by the following claims and their equivalents.

What is claimed is:

1. An implantable heart rhythm management device comprising:
    one or more leads for sensing electrical signals of a patient or for applying electrical energy to the patient;
    a monitoring circuit for monitoring heart activity of the patient through one or more of the leads; and
    a therapy circuit for delivering electrical energy through one or more of the leads to a heart of the patient, wherein the therapy circuit includes one or more wet electrolytic capacitors, each comprising:
        a rolled capacitive element, the capacitive element including at least first and second metallic foils and at least one electrolyte impregnated separator between the foils; and
        first and second conductive endcaps electrically coupled to the respective first and second metallic foils, with each endcap having a concave surface at least partially enclosing an end of the rolled capacitive element.

2. The implantable heart rhythm management device of claim 1, wherein the first and second endcap include respective first and second tubular portions which encircle respective portions of the rolled capacitive element.

3. The implantable heart rhythm management device of claim 1, further including an insulative tube having a first end abutting the first conductive endcap and a second end abutting the second conductive endcap.

4. The implantable heart rhythm management device of claim 1, wherein the device is a defibrillator.

5. The implantable heart rhythm management device of claim 1, wherein each concave surface is substantially hemispherical.

6. An implantable heart rhythm management device comprising:
    one or more leads for sensing electrical signals of a patient or for applying electrical energy to the patient;
    a monitoring circuit for monitoring heart activity of the patient through one or more of the leads; and
    a therapy circuit for delivering electrical energy through one or more of the leads to a heart of the patient, wherein the therapy circuit includes one or more wet electrolytic capacitors, each comprising:
        a rolled capacitive element, the capacitive element including at least first and second metallic foils and at least one electrolyte impregnated separator between the foils; and
        first and second means for at least partially enclosing respective end portions of the rolled capacitive element.

7. The implantable heart rhythm management device of claim 6, wherein the first and second means are electrically coupled to the respective first and second metallic foils.

8. The implantable heart rhythm management device of claim 6, wherein the device includes a defibrillator.

9. The implantable heart rhythm management device of claim 6 wherein the metallic foils comprise aluminum.

10. An implantable heart rhythm management device comprising:
    one or more leads for sensing electrical signals of a patient or for applying electrical energy to the patient;
    a monitoring circuit for monitoring heart activity of the patient through one or more of the leads; and
    a therapy circuit for delivering electrical energy through one or more of the leads to a heart of the patient, wherein the therapy circuit includes one or more wet electrolytic capacitors, each comprising:
        a rolled capacitive element, the capacitive element including at least first and second metallic foils and at least one electrolyte impregnated separator between the foils; and
        first and second conductive endcaps, with each endcap having a concave surface at least partially enclosing an end of the rolled capacitive element.

11. The implantable heart rhythm management device of claim 10, wherein the first and second endcaps include respective first and second tubular portions which encircle respective portions of the rolled capacitive element.

12. The implantable heart rhythm management device of claim 10, further including an insulative tube having a first end abutting the first conductive endcap and a second end abutting the second conductive endcap.

13. The implantable heart rhythm management device of claim 10, wherein the first conductive endcap is electrically coupled to the second conductive endcap.

14. The implantable heart rhythm management device of claim 10:
    wherein the first and second endcaps include respective first and second holes; and
    wherein the device further comprises:
        a first feedthrough conductor extending through the first hole and electrically coupled to the first metallic foil; and
        a second feedthrough conductor extending through the second hole and electrically coupled to the second metallic foil.

15. The implantable heart rhythm management device of claim 10, wherein the device includes a defibrillator.

16. An implantable heart rhythm management device comprising:
    one or more leads for sensing electrical signals of a patient or for applying electrical energy to the patient;
    a monitoring circuit for monitoring heart activity of the patient through one or more of the leads; and
    a therapy circuit for delivering electrical energy through one or more of the leads to a heart of the patient, wherein the therapy circuit includes one or more wet electrolytic capacitors, each comprising:
        a capacitive element including at least first and second metallic foils and at least one electrolyte impregnated separator between the foils; and
        first and second means for at least partially enclosing respective end portions of the rolled capacitive element.

17. The implantable heart rhythm management device of claim 16, wherein the metallic foils each comprises aluminum.

* * * * *